United States Patent [19]

Biscoping et al.

[11] Patent Number: 5,135,525
[45] Date of Patent: Aug. 4, 1992

[54] CATHETER SET FOR CONTINUOUS SPINAL ANAESTHESIA

[75] Inventors: Juergen Biscoping, Giessen; Marie L. Summerer; Hans H. Witt, both of Koerle, all of Fed. Rep. of Germany

[73] Assignee: B. Braun Melsungen AG, Melsungen, Fed. Rep. of Germany

[21] Appl. No.: 532,053

[22] Filed: Jun. 1, 1990

[30] Foreign Application Priority Data

Jun. 6, 1989 [DE] Fed. Rep. of Germany ....... 3918431

[51] Int. Cl.⁵ ..................... A61M 31/00; A61M 5/178
[52] U.S. Cl. ...................................... 604/51; 604/117; 604/166; 606/186
[58] Field of Search ............... 604/164, 165, 166, 167, 604/51, 170, 50, 169, 168, 158-163, 171, 117, 27-28, 264, 266-267, 274; 128/753, 754; 606/186

[56] References Cited

U.S. PATENT DOCUMENTS

| | | | |
|---|---|---|---|
| 2,623,521 | 12/1952 | Shaw | 604/170 |
| 2,919,692 | 1/1960 | Ackermann | 128/754 |
| 3,459,189 | 7/1965 | Alley | 604/166 |
| 3,539,034 | 10/1966 | Tafeen | 604/164 |
| 3,630,198 | 12/1971 | Henkin | 604/166 |
| 3,719,737 | 3/1973 | Vaillancourt et al. | 604/281 |
| 3,788,320 | 1/1974 | Dye | 604/165 |
| 3,941,127 | 3/1976 | Froning | 604/51 |
| 4,349,023 | 9/1982 | Gross | 604/164 |
| 4,518,383 | 5/1985 | Evans | 604/51 |
| 4,573,448 | 10/1983 | Kambin | 604/51 |
| 4,668,221 | 5/1987 | Luther | 604/166 |
| 4,737,146 | 4/1980 | Yoshikiyo | 604/51 |
| 4,940,458 | 7/1990 | Cohn | 604/117 |
| 4,973,312 | 11/1990 | Andrew | 604/165 |
| 4,994,036 | 2/1991 | Biscoping | 604/51 |

Primary Examiner—C. Fred Rosenbaum
Assistant Examiner—Mark Bockelman
Attorney, Agent, or Firm—Spensley, Horn, Jubas & Lubitz

[57] ABSTRACT

A catheter set including an epidural cannula having a dull leading end; i.e., a leading end without a cutting grinding. A first trocar, only the tip of which projects beyond the epidural cannula, may be inserted into the epidural cannula for puncturing. The leading end of the epidural cannula may abut against the dura without the dura being perforated by the tip of the trocar. Thereafter, the first trocar may be removed and the dura may be punctured by a second trocar which is longer than the first trocar and which may be inserted into the cannula. After removal of the second trocar, a catheter may be inserted through the punctured dura into the spinal area, using the epidural cannula as a guide cannula. The puncture caused by the second trocar is entirely closed by the catheter. This opening remains small, since the epidural cannual has no grinding to cut the dura.

4 Claims, 3 Drawing Sheets

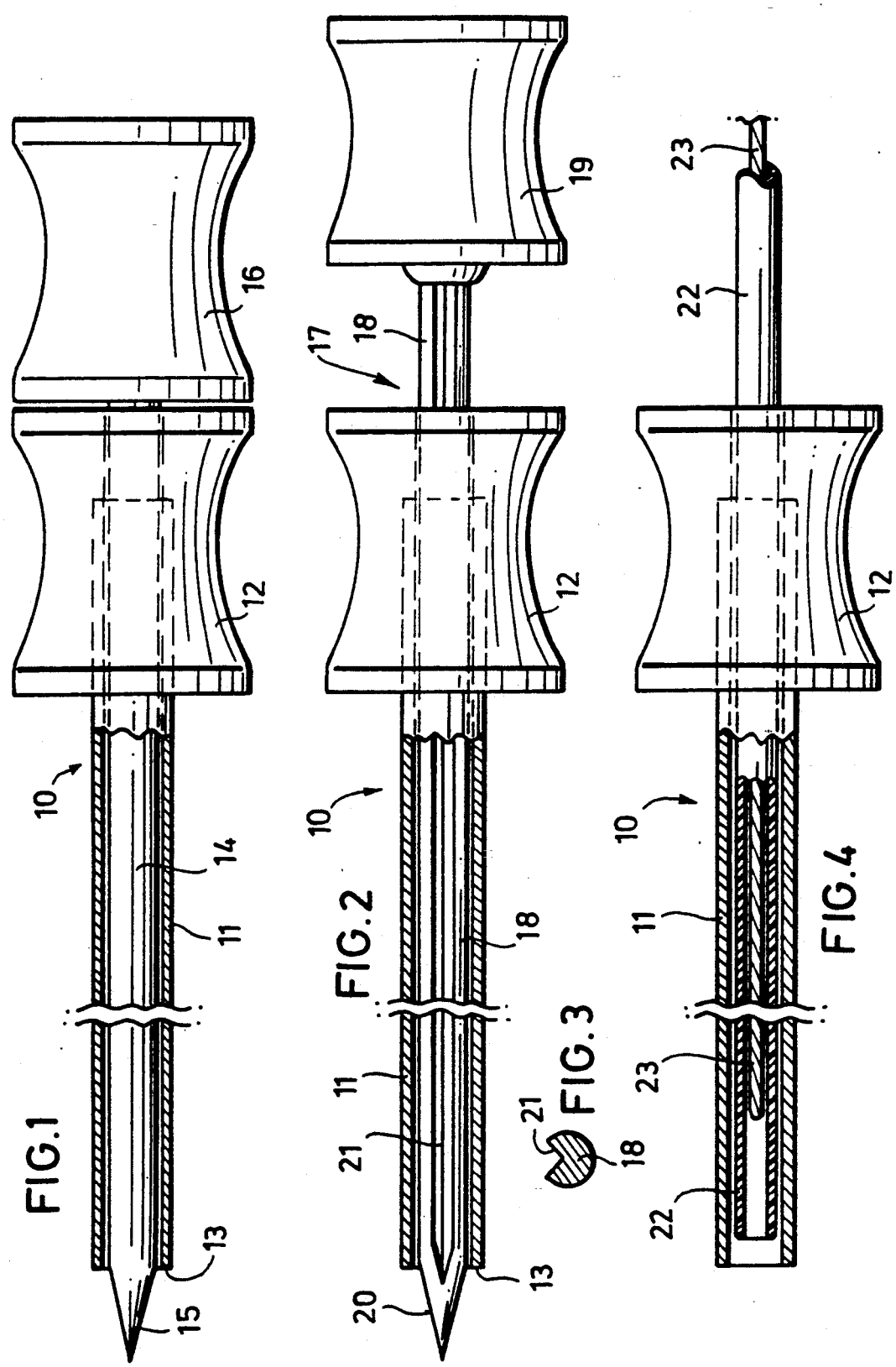

CATHETER SET FOR CONTINUOUS SPINAL ANAESTHESIA

BACKGROUND OF THE INVENTION

1. Field of the Invention

The invention relates to a catheter set for continuous spinal anaesthesia.

2. Description of Related Art:

In continuous spinal anaesthesia, a catheter of small diameter is introduced into the area of the spine. However, problems may arise due to puncturing of the dura. In order to minimize damage of the dura and the post-spinal headaches resulting therefrom, catheters with a minimum outer diameter have been used. On the other hand, up to the present, puncturing the dura has required the use of a puncture cannula through which a thin catheter is subsequently advanced, whereupon the puncture cannula is removed. Since the hole in the dura caused by the puncture cannula is larger than the diameter of the catheter, liquor flows past the catheter through the hole in the dura. This results in a high loss of liquor with possible accompanying post-spinal headaches.

German Utility Mode 88 11 408 U1 (U S. Pat. application Ser. No. 07/390,608), now U.S. Pat. No. 4,994,036 describes a catheter device for spinal anaesthesia which includes an epidural cannula that is advanced up to the dura. A spinal cannula that is longer than the epidural cannula may be inserted into the epidural cannula, the leading end of the spinal cannula carrying a tip for puncturing the dura. First, a mandrin is introduced into the spinal cannula over which the catheter is subsequently advanced after the removal of the spinal cannula according to the Seldinger-method. The diameter of the catheter is substantially the same as that of the resulting hole in the dura, so that the size of the hole in the dura is limited to a minimum. However, the catheter device described above requires a relatively complicated method of insertion.

It is an object of the present invention to provide a catheter set which can be handled easily and which reduces the possible damage to the dura to a minimum.

SUMMARY OF THE INVENTION

In accordance with the present invention, this and other objectives are achieved by providing a catheter set in which the epidural cannula has a dull leading end; i.e., it has no cutting grinding, so that it will abut the dura with the dull end without damaging the dura. The puncture is performed with a trocar that sits within the epidural cannula from which only its front tip projects. The trocar has a conical tip and no cutting edge. This tip penetrates the tissue of the ligamentum supra- and interspinale without severing the fibers. When the epidural cannula reaches the ligamentum flavum, the trocar may be pulled out and the epidural space may be identified; e.g., by means of the "loss-of-resistance" method. Then, the epidural cannula may be advanced for a few mm. Upon reaching the dura, the epidural cannula will not penetrate the dura, but rather will abut against the dura, while being slightly advanced. Due to the dull leading end, the epidural cannula is not able to enter the dura, but merely forms a guide channel extending to the dura.

Subsequently, the dura may be punctured by means of a second trocar, suitably provided for this purpose, which is longer than the first trocar and which has substantially the same diameter. This second trocar, which also has a non-cutting tip, may be advanced intrathecally and subsequently withdrawn in order to be able to introduce the catheter thereafter.

A second possibility is to advance a catheter within the epidural cannula extending up to the dura, in which cannula a mandrin may be provided, the conical tip of which projects from the catheter by about 1 to 2 mm. When advancing the catheter, the wire mandrin stabilizes the catheter and perforates the dura together with the enclosing catheter.

In any case, the hole in the dura is not larger than the outer diameter of the catheter so that the hole in the dura will tightly surround the catheter and the amount of liquor oozing therefrom may be limited to a minimum amount.

BRIEF DESCRIPTION OF THE DRAWINGS

A detailed description of a preferred embodiment of the invention will be made with reference to the accompanying drawings.

FIG. 1 shows a side elevational view of an epidural cannula, partially cut, with a first trocar provided, FIG. 2 shows a side elevational view of an epidural cannula, partially cut, with a second trocar inserted, FIG. 3 shows a section of a second trocar, FIG. 4 shows a longitudinal section of an epidural cannula with a catheter inserted.

Figure 5:
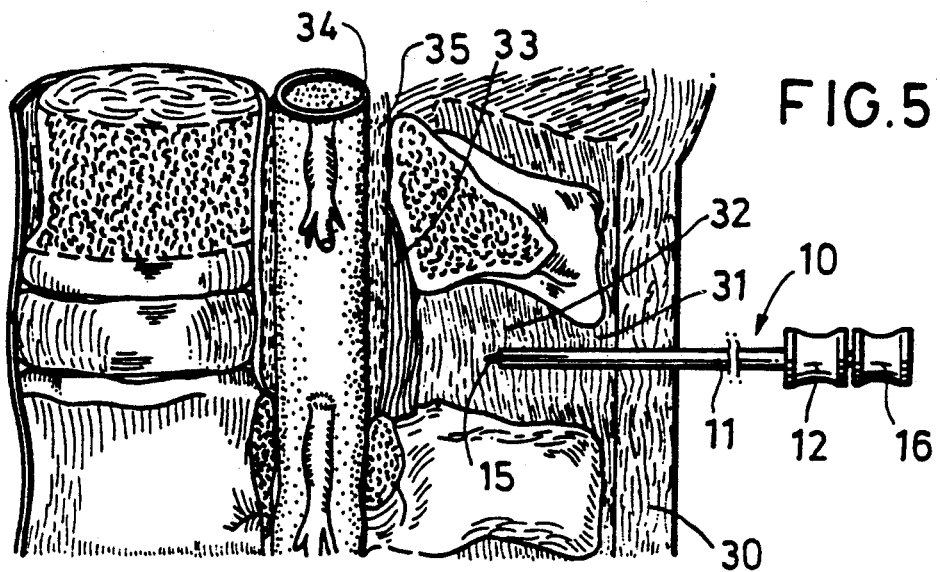
FIG. 5 to 8 show the different stages of an application of a catheter set.

DETAILED DESCRIPTION OF PREFERRED EMBODIMENTS:

The following detailed description is of the best presently contemplated mode of carrying out the invention. This description is not to be taken in a limiting sense, but is made merely for the purpose of illustrating the general principles of the invention. The scope of the invention is best defined by the appended claims.

The catheter set has an epidural cannula 10 consisting of a cannula tube 11 and a handle piece 12 (or cannula hub). The leading end 13 of the cannula tube 11 terminates in a dull tip; i.e., without a cutting grinding. The leading end 13 need not extend at right angles to the longitudinal direction of the cannula 10, but may be slightly slanted if the cannula is designed to be introduced to the dura at an angle of less than 90°. Moreover, the leading end 13 may be rounded or slightly conically bevelled outward. The cannula tube 11 preferably has dimensions of e.g.; $0.7 \times 0.9 \times 80$ mm, the first number indicating the inner diameter, the second number indicating the outer diameter and the third number giving the free length of the cannula tube 11.

The channel of the cannula tube 11 extends through handle piece 12. The first trocar 14 may be inserted into the epidural cannula 10. The trocar consists of a rod of a solid material having its front end provided with a symmetrical tip 15, preferably having a maximum length of about 2mm. With the trocar 14 fully inserted, i.e., when the handle piece 16 of the trocar abuts the handle piece 12 of the epidural cannula, only the tip 15 of the trocar will project beyond the front end of the cannula tube 11. The tip 15 of the trocar may also have a pyramidal shape or be provided with an asymmetrical grinding.

Figure 6:
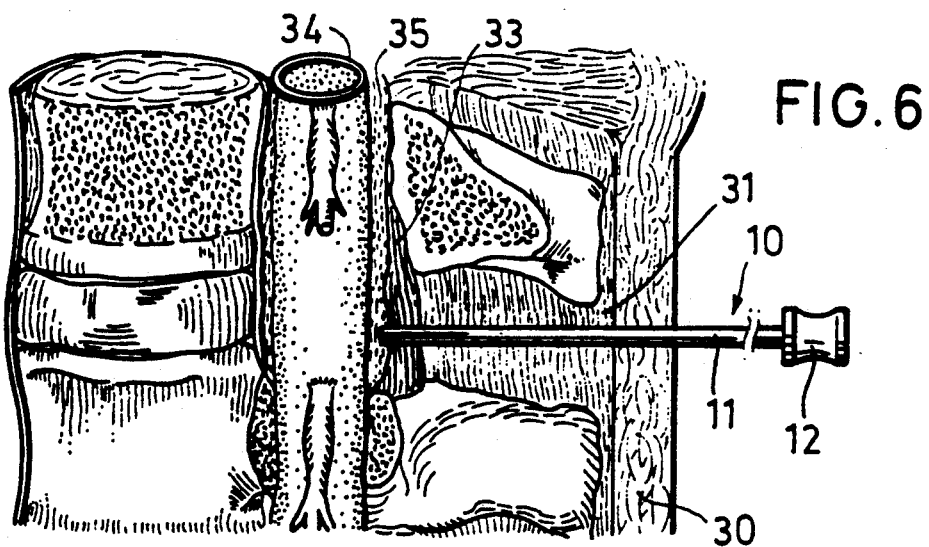

As shown in FIG. 5, the device may be introduced through the skin 30 of a patient in the state depicted in FIG. 1, the tip 15 serving for the puncturing. First, the ligamentum supraspinal 31 is passed, then the ligamentum intraspinal 32 is passed, until the ligamentum flavum 33 is reached. The trocar 14 may be then removed and, when the user has identified the peridural space 35 by means of the cannula 10, the device will be advanced (in the case of adults) for another 5 to 7 mm (FIG. 6) in order to penetrate the peridural space 35. With a high degree of certainty, the dull tip 13 will then abut the dura 34, which will be slightly deformed thereby (FIG. 7).

According to FIG. 2, a second trocar 17 may be provided consisting of a solid rod 18 and a handle piece 19. At the leading edge of the rod 18, a symmetrical point 20 may be arranged that is principally shaped in the same way as the tip 15 of the first trocar 14. The penetration length of the second trocar 17 may be about 15 mm longer than that of the puncture cannula 10 (and the first trocar 14) so that, with the second trocar 17 fully inserted in the epidural cannula, not only the point 20 but also a section of the rod 18 will project from the cannula tube 11.

Figure 7:
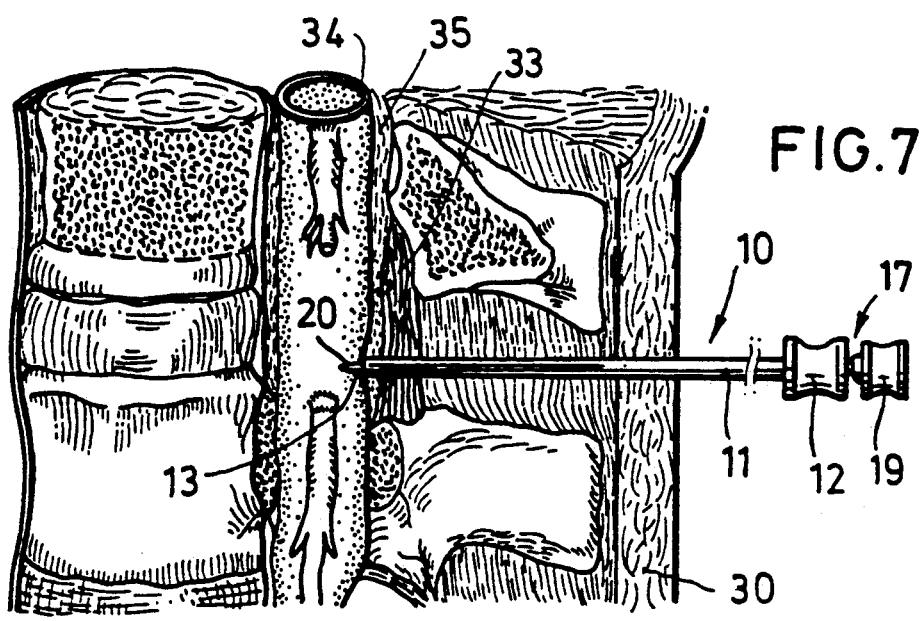

FIG. 7 shows the device in the state of FIG. 2, after the second trocar 17 has been advanced to the end stop, the point 20 having pierced the dura.

The second trocar 17 has a through-going longitudinally extending channel 21 which, in the preferred embodiment, is formed as an open groove or notch with an aperture angle of about 80 to 90°. Liquor may drain from this notch, thereby indicating a successful puncturing of the dura.

Figure 8:
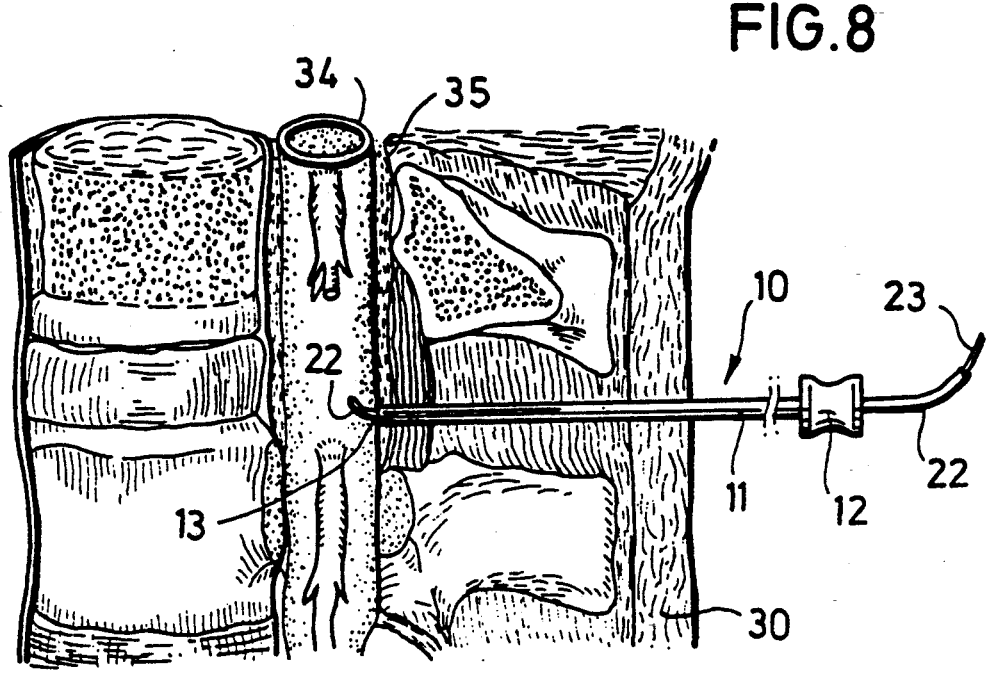

After the puncture has been made, the second trocar 17 may be removed from the epidural cannula 10 and the catheter 22, with a mandrin 23 located therein, may be advanced through the epidural cannula 10 into the area of the spine (FIG. 8). If the catheter is rigid enough to be advanced, a mandrin 23 need not be provided.

The puncture opening in the dura caused by the second trocar 17 is entirely closed by the catheter 22. The opening is small, since the cannula does not have a grinding that would cut the dura and since the cannula does not penetrate the dura.

The mandrin 23 of the spinal catheter 22 begins about 1 to 2 mm behind the front tip of the catheter so that only the comparatively soft catheter tip will reach the opening in the dura and the spinal area therethrough. Subsequently, the mandrin 23 may be withdrawn.

FIG. 8 shows how the catheter 22 may be inserted. Next the mandrin 23 may be pulled out and, finally, the epidural cannula 10 may be pulled from the patient's body over the set catheter.

Figure 9:
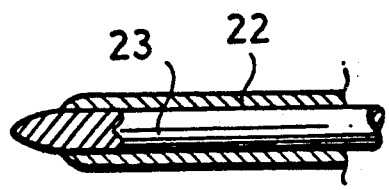
FIG. 9 shows another way to use a catheter set.

An experienced user will not inevitably need to use the second trocar 17. After the peridural space 35 has been found (see FIG. 6), the catheter 22 with the mandrin 23 may be inserted into the cannula, as shown in FIG. 8, the leading tip of the mandrin projecting from the catheter 22, as illustrated in FIG. 9. In this case, the puncture of the dura may be performed with the projecting tip of the mandrin. After the dura has been punctured, the catheter 22 may be advanced over the mandrin 23, the mandrin and the cannula being subsequently withdrawn.

What is claimed is:

1. A catheter set for spinal anesthesia, comprising:
   a cannula having a substantially dull leading end,
   a solid trocar having a solid tip for puncturing skin and muscle tissue up to the dura, the trocar being adapted for insertion into the cannula, the trocar and the cannula being mutually configured so that substantially only the tip of the trocar projects beyond the leading end of the cannula when the trocar is inserted into the cannula,
   dura-perforating means having a solid tip for piercing the dura, the dura-perforating means being adapted for insertion into the cannula, and
   a catheter adapted for advancement through the cannula,
   whereby the substantially dull leading end of the cannula prevents the cannula from entering and damaging the dura enclosing the spinal channel,
   wherein the trocar comprises a first trocar having a length and a diameter, and wherein the dura-perforating means comprises a second trocar adapted for insertion into the cannula, the second trocar having a length which is greater than the length of the first trocar and having a diameter which is substantially equal to the diameter of the first trocar, and
   wherein the second trocar comprises a solid trocar having a solid tip and a longitudinally extending liquor channel terminating behind the solid tip of the second trocar.

2. The catheter set according to claim 1, wherein the second trocar includes a symmetrical non-cutting tip.

3. The catheter set according to claim 1, wherein the trocar comprises a first trocar and further comprising:
   a second trocar having a tip and being adapted for insertion into the cannula, the second trocar and the cannula being mutually configured so that substantially more than the tip of the second trocar projects beyond the leading end of the cannula when the second trocar is inserted into the cannula.

4. A method of delivering anesthetic to a spinal channel, comprising the steps of:
   providing a cannula having a substantially dull leading end,
   inserting a first solid trocar having a solid tip into the cannula, the first trocar and the cannula being mutually configured so that substantially only the tip of the first trocar projects beyond the leading end of the cannula when the first trocar is inserted into the cannula,
   advancing the cannula through skin and muscle tissue to the peridural space,
   withdrawing the first trocar from the cannula,
   inserting a second solid trocar having a solid tip into the cannula, the second trocar and the cannula being mutually configured so that substantially more than the tip of the second trocar projects beyond the leading end of the cannula when the second trocar is inserted into the cannula,
   puncturing the dura with he second trocar,
   withdrawing the second trocar from the cannula,
   advancing a catheter through the cannula into the spinal channel, and
   delivering anaesthetic through the catheter to the spinal channel.

* * * * *